(12) United States Patent
Costa

(10) Patent No.: US 6,403,075 B1
(45) Date of Patent: Jun. 11, 2002

(54) ODOR SUPPRESSION IN AMMONIA-CONTAINING COSMETIC PRODUCTS

(75) Inventor: Jill Costa, Goshen, NY (US)

(73) Assignee: Dragoco Gerberding & Co. AG (DE)

( * ) Notice: Subject to any disclaimer, the term of this patent is extended or adjusted under 35 U.S.C. 154(b) by 0 days.

(21) Appl. No.: 09/526,169

(22) Filed: Mar. 15, 2000

(51) Int. Cl.$^7$ ................ A61L 9/00; A61L 9/01; A61K 7/135; A61K 7/06
(52) U.S. Cl. .............. 424/76.1; 424/400; 424/401; 424/62; 424/70.1; 514/880
(58) Field of Search .................. 514/111, 114, 514/227, 236, 312, 510, 513, 538; 424/400, 401, 70.1, 70.2, 70.6, 76.1, 62

(56) References Cited

U.S. PATENT DOCUMENTS

| | | | | |
|---|---|---|---|---|
| 5,554,363 A | * | 9/1996 | Nandairi et al. ......... | 424/70.51 |
| 5,554,364 A | * | 9/1996 | Neill et al. ............. | 424/76.1 |
| 5,786,367 A | * | 7/1998 | Oshiro et al. ........... | 514/312 |
| 6,024,768 A | * | 2/2000 | Bittner et al. .......... | 8/410 |

* cited by examiner

Primary Examiner—Thurman K. Page
Assistant Examiner—Charesse L. Evans
(74) Attorney, Agent, or Firm—Pendorf & Cutliff

(57) ABSTRACT

A method and composition are disclosed with which it becomes possible to reduce the perception of ammonia odor in ammonia-containing compositions such as hair bleaches and colorants. A perfume composition containing at least one perfume material which is olfactively stable in the ammonia base and satisfies one of the following criteria is added to the ammonia-containing composition:

(1) contains a phenyl ring moiety and has an air diffusion coefficient of >5.7, (2) contains a C-5 ring moiety, which also contains at least 1 carbon which is sp2 hybridized, and has an air diffusion coefficient of >4.4.

8 Claims, No Drawings

ODOR SUPPRESSION IN AMMONIA-CONTAINING COSMETIC PRODUCTS

BACKGROUND OF THE INVENTION

1. Field of the Invention

The present invention concerns reduction of the perception of ammonia odor in ammonia containing compositions such as hair bleaches and colorants.

2. Discussion of the Related Art

Many hair treatment compositions contain ammonia and are characterized by an offensive odor.

For example, hair-bleaching agents based on a peroxide oxidation agent, such as hydrogen peroxide, urea peroxide, melamine perhydrate, etc. are generally used for the bleaching of human hair. The action of aqueous hydrogen peroxide solution per se, even under alkaline conditions, is too slow, so that hair damage may occur. Aqueous ammonia is an effective activator for the hair bleaching action of aqueous peroxide solutions, accelerating the oxidative destruction of the particles of the hair pigment (melanosomes), speeding up the rate at which the hair pigments are oxidized. It has therefore been customary to use ammonia in bleaching compositions for this purpose.

In addition, the pH of the aqueous hydrogen peroxide solutions must be adjusted to the alkaline side if they are to serve as effective bleaching agents for hair. Although the pH effect is different from the activator effect of ammonia (since the pH effect can be accomplished with alkaline materials other than ammonia), it has been common practice to use ammonia both for its activator effect and for its pH adjusting effect on the composition. As a consequence, with a few exceptions, essentially all the commercial hair bleaching compositions contain substantial quantities of ammonia.

Further, in hair dyes, the color vehicle for the dye intermediates is employed at a pH usually between about 9 and 11. Adjustment of pH to the desired level of alkalinity can be accomplished with ammonium hydroxide. The ammonium hydroxide base is preferred since ammonia assists in swelling the hair fiber and is easily removed.

Unfortunately, the presence or evolution of ammonia results in a particularly disagreeable strong ammonia odor. It is generally accepted that the unpleasant odor of ammonia cannot be masked even by perfuming.

Accordingly, efforts have been made in the prior art to provide ammonia-free hair bleaching compositions. One such attempt is described in U.S. Pat. No. 2,283,350. This patent describes the use of aliphatic amines or alkanolamines in place of ammonia or ammonium hydroxide to avoid the unpleasant ammonia odor. However, in this case, the resulting bleach mixture is more damaging (for the same degree of lightening) to the keratin hair fibers.

Another attempt at providing an ammonia-free hair bleach composition can be found in the U.S. Pat. No. 3,816,615 to Zeffern et al. In this case, activation of the peroxide oxidizing agent is accomplished by means of certain dicarbonyl compounds. In place of ammonium hydroxide, the patentees employ certain guanidine salts. This approach has not received any wide acceptance in the industry, which is probably due to the fact that the hair damage encountered in the use of the amines noted above is also encountered with the guanidine compounds.

Another approach to the odor problem has been to replace ammonia by odorless alkalinization agents such as alkali metal hydroxides, magnesium oxide or by alkanolamines, and to further accelerate the bleaching process in order to avoid the disadvantages of ammonia on the one hand and, on the other hand, to minimize the oxidative damage to the hair. U.S. Pat. No. 4,226,852 (Tesmann, et al.) teaches a two-component composition for bleaching hair comprising a peroxide oxidation agent, an ammonia-free alkalinization agent, and a guanidine derivative as bleaching accelerator. Unfortunately, guanidine derivatives are associated with hair damage.

A water insoluble gel is generally used to keep the bleach mixture on the hair fibers and prevent it from running or creeping away from the hair shaft and to run down off the head. The use of water-insoluble surfactants (see U.S. Pat. No. 2,283,350 for the use of high molecular weight alcohols for this purpose), however, greatly affects the lightening ability of the bleach mixture. To overcome reduced bleaching activity, high levels of ammonia are required. In conventional gels, the ammonia contained in the hair dye compositions is quickly given off from the gels to the environment, causing an odor problem. A loss of ammonia in the hair dye composition also lessens the covering power of the dyes, especially on gray hair. The same is essentially true of compositions that employ water-insoluble thickening agents. These also require relatively high levels of ammonia to raise the activity of the bleach composition to a suitable level.

U.S. Pat. No. 4,507,278 (DeMarco, et al.) teaches that, by utilizing water-soluble surfactant thickening agents, it is possible to dispense with the need for using ammonia as an activator. In this case, a non-ammonia alkalizing agent, and preferably one which does not have the potentiality for hair damage, can be employed to give the composition its appropriate pH. However, when only water-soluble surfactant thickening agents are employed, the viscosity of the product when it is applied to the head is too low for satisfactory application of the bleach. On the other hand, when an effort was made to increase the viscosity by the addition of water-insoluble surfactant thickening agents, it was found that the effectiveness of the bleaching composition, i.e., the rate at which the bleaching action occurred, was reduced to an unacceptable level. It was discovered that if a small quantity of ammonia is present in the composition (no greater than 0.55% by weight based on the total weight of the composition measured as ammonium ion concentration) and the ratio of water-soluble to water-insoluble surfactant thickener was maintained in the range of from 1.8 to 7.0, a highly effective product is obtained having the requisite level of bleaching activity, a suitable viscosity in use for application of the bleach, and substantially no ammonia odor.

Nevertheless, most hair coloring products in general use continue to be comprised of aqueous solutions with up to about 8% ammonia. Ammonia odors emanating from the coloring composition are difficult to mask and can be offensive to the hair color user.

There is thus a need for a method for the suppression of the ammonia odor in an ammonia-containing hair colorant.

SUMMARY OF THE INVENTION

The general understanding in the art is that ammonia odors are too intense to be masked by a perfume composition.

The present invention began by undertaking an investigation which ran contrary to this conventional wisdom. After extensive testing, it was surprisingly found that the perception of reduced ammonia odor does not depend on the maskant material's odor detection threshold or on the perceived inherent intensity of the maskant material. Rather, it was found that the perception of the ammonia odor can be lessened by use of maskant materials with a high air diffusion coefficient.

Perfumes containing at least 25% of materials satisfying the criteria of the invention can be expected to cover the perception of ammonia better than those which do not.

The foregoing has outlined rather broadly the features and technical advantages of the present invention in order that the detailed description of the invention that follows may be better understood. Additional features and advantages of the invention will be described hereinafter which form the subject of the claims of the invention.

DETAILED DESCRIPTION OF THE INVENTION

Typically, perfumes are created for hair colors or bleaching compositions by selecting materials known to be stable in the systems. The present inventor amassed a large collection of such perfumes.

Materials listed in Table 1 were tested for stability in an 8% ammonia system. Materials were dosed at 1% into the ammonia base. Solids were made into a 10% dilution and dosed at 1%. The materials were evaluated for ammonia coverage, olfactive odor stability, and visual physical appearance (color, cloudiness) at 1, 2, and 3 weeks, and at 5° C., 25° C., and 38° C. The materials were not solubilized for the raw material study. Full results were tabulated and are presented in Table 2.

A list of the air diffusion coefficients for the materials studied is set forth in Table 3.

After subjecting the materials to a variety of tests and recording the results on a table for comparative analysis, it was discovered that the ability of a material to mask the perception of ammonia from an aqueous media can be predicted using the following criteria, wherein suitable materials fall into two groups:

Group 1: Materials falling into this category are expected to mask the perception of ammonia if they:
1. Are olfactively stable in the ammonia base—i.e., these materials may change but do not degrade to a sharp, green aldehydic character.
2. Contain a phenyl ring moiety.
3. Have an air diffusion coefficient of >5.7.

Group 2: Materials falling into this category are expected to mask the perception of ammonia if they:
1. Are olfactively stable in the ammonia base—i.e., these materials may change but do not degrade to a sharp, green aldehydic character.
2. Contain a C-5 ring moiety, which also contains at least 1 carbon which is sp2 hybridized.
3. Have an air diffusion coefficient of >4.4.

Perfumes containing at least 25W of materials of Group I and/or Group II can be expected to cover the perception of ammonia better than those which do not.

TABLE I

| Material | Dragoco Number | Test Group |
| --- | --- | --- |
| ETHYL ACETOACETATE | 4/910050 | 1 |
| HEXYL CINNAMIC ALDEHYDE | 3/011371 | 1 |
| LILIAL | 4/929325 | 1 |
| ORANGE OIL FLORIDA | 4/777160 | 1 |
| DIOLA | 3/926899 | 1 |
| PHENYL ETHYL ALCOHOL | 3/964540 | 2 |
| ISO BORNYL ACETATE | 3/943760 | 2 |
| ISO E SUPER | 0/115115 | 2 |
| TETRAHYDRO LINALOOL | 4/901360 | 2 |
| FLORAZONE | 3/034395 | 2 |
| DIHYDRO TERPINEOL | 4/016236 | 3 |
| METHYL IONONE GAMMA | 4/931205 | 3 |
| YLANAT | 3/084021 | 3 |
| YLANAT ORTHO | 3/084027 | 3 |
| MELONAL | 3/054211 | 3 |
| ALLYL CYCLOHEXYL PROPIONATE | 3/011241 | 4 |
| CYCLOHEXYL ETHANOL | 3/924060 | 4 |
| FLOROL | 3/934060 | 4 |
| GERANYL ACETATE | 3/039991 | 4 |
| PRENYL ACETATE | 3/026832 | 4 |
| ROSEMARY OIL TUNISIA | 1/510706 | 5 |
| CRESSANTHER | 3/045062 | 5 |
| PETIOLE | 4/780162 | 5 |
| YSAMBER K | 3/055120 | 5 |
| ALLYL HEPTOATE (C-7) | 4/010500 | 5 |
| ANTHER | 3/912100 | 6 |
| EUCALYPTUS GLOBULUS | 1/913422 | 6 |
| MAYOL | 3/954401 | 6 |
| CEDRAMBER | 3/018911 | 6 |
| CEDROL LIQUID | 3/019281 | 6 |
| TONALID | 3/976500 | 7 |
| GALAXOLIDE 50 DEP | 4/900551 | 7 |
| PHENAFLEUR | 3/964150 | 7 |
| TRIDECENE-2-NITRILE | 3/076791 | 7 |
| CLONAL | 3/923790 | 7 |
| VELOUTONE | 4/949088 | 8 |
| METHYL NAPTHYL KETONE | 4/933020 | 8 |
| NEROLIN YARA YARA | 3/959050 | 8 |
| SANDRANOL | 3/070540 | 8 |
| CISTULATE 09126 | 3/920335 | 8 |
| PADMA | 3/064461 | 9 |
| METHYL CHAVICOL | 4/131155 | 9 |
| RHUBAFURAN | 4/941135 | 9 |
| RHUBOFIX | 3/971450 | 9 |
| DELPHONE, FIRMENICH | 4/916128 | 9 |
| GRAPEFRUIT BASE 15.794 B | 0/115317 | 10 |
| ORANGE JUICE CARBONYLS | 4/777119 | 10 |
| CAMPHENE | 4/726750 | 10 |
| BENZALDEHYDE | 3/914590 | 10 |

|  |  |  | 1 Week, 5 C | | | 2 Week, 5 C | | | 3 Week, 5 C | | |
| --- | --- | --- | --- | --- | --- | --- | --- | --- | --- | --- | --- |
| Material | Number | % | Color/ Physical | RM Odor | NH3 Coverage | Color/ Physical | RM Odor | NH3 Coverage | Color/ Physical | RM Odor | NH3 Coverage |
| Orange Oil Florida | 4/777160 | 1.0% | As RM, 8 mm Cloudy Top | OK | 2 | OK, 8 mm Cloudy Top | flat citrus | 3 | OK, hazy | aldehydic, orange, caraway | 2 |
| Diola | 3/926899 | 1.0% | OK, sl. Swirly cloudiness | OK | 5 | Ok, Clear | banana, green | 4 | OK, Clear | green, banana, fruity | 4 |
| Ethyl Acetoacetate | 4/910050 | 1.0% | OK, Clear | OK | 3 | OK, Clear | sour, weak | 2 | OK, Clear | pungent, rancid | 1 |
| Lilial | 4/929325 | 1.0% | OK, Clear | Oxidized | 2 | OK, Clear | Flora, oxidized | 3 | OK, Clear | sour, oxidized | 2 |
| Hexyl cinnamic Aldehyde | 3/011731 | 1.0% | OK, 3 mm cloudy top | Changed | 2 | OK, Hazy throughout | floral, jasmin | 3 | OK, hazy | low | 2 |
| Tetrahydro-linalool | 4/901360 | 1.0% | OK, 5 mm Cloudy Top | OK | 2 | OK, 3 mm cloudy top | floral, green | 3 | OK, cloudy | floral | 3 |
| Florazone | 3/034395 | 1.0% | OK, Clear | OK | 5 | OK, Clear | green, sl. Sour plastic | 4 | OK, Clear | floral ozone, green | 3 |
| Iso E Super | 0/115115 | 1.0% | OK, Clear | OK | 2 | OK, 3 mm cloudy top | woody, floral | 4 | OK, cloudy | sl. Sour, woody | 2 |
| Iso Bornyl Acetate | 3/943760 | 1.0% | OK, 8 mm Cloudy Top | OK | 3 | OK, 5 mm Cloudy top | woody, borneol | 4 | OK, 10 mm cloudy | borneol, isobornyl ace | 3 |
| Phenyl Ethyl Alcohol | 3/964540 | 1.0% | OK, Clear | OK | 4 | OK, Clear | rose, floral | 5 | OK, Clear | rosy | 4 |
| Dihydro Terpineol | 4/016236 | 1.0% | OK, 5 mm Cloudy Top | OK | 3 | OK, 2 mm cloudy | sour, terpineol | 2 | OK, 2 mm cloudy | floral, green, sour | 3 |
| Ylanat Ortho | 3/084027 | 1.0% | OK, 5 mm Cloudy Top | Woody/ Green | 3 | OK, 5 mm Cloudy top | sour, sharp, green | 2 | OK, 5 mm cloudy | woody, sharp green | 3 |
| Ylanat | 3/084021 | 1.0% | OK, 5 mm Cloudy Top | OK | 3 | OK, 8 mm Cloudy top | sour, sharp | 2 | OK, 5 mm cloudy | woody, sharp green | 3 |
| Melonal | 3/054211 | 1.0% | OK, Clear | Sour, Acidic | 2 | OK, Clear | plasticky, melon | 1 | OK, Clear | plastic, sour | 2 |
| Methyl Ionone Gamma | 4/931205 | 1.0% | OK, 5 mm Cloudy Top | OK | 4 | OK, 3 mm cloudy top | woody | 3 | oK, 3 mm cloudy | ionone | 3 |
| ALLYL CYCLOHEXYL PROPIONATE | 3/011241 | 1.0% | OK, 8 mm Cloudy Top | OK | 2 | OK, Clear | pineapple | 3 | OK, 1 mm cloudy | pineapple, fruity | 2 |
| CYCLOHEXYL ETHANOL | 3/924060 | 1.0% | OK, 5 mm Cloudy Top | OK | 1 | OK, Clear | floral, green, plastic | 3 | OK, 4 mm cloudy | green, waxy floral | 2 |
| FLOROL | 3/934060 | 1.0% | OK, Clear | OK | 3 | OK, Clear | floral, muguet | 4 | OK, Clear | jasmine, floral | 2 |
| GERANYL ACETATE | 3/039991 | 1.0% | OK, 5 mm Cloudy Top | OK | 3 | OK, Clear | weak geraniol | 1 |  |  |  |
| PRENYL ACETATE | 3/026832 | 1.0% | OK, Clear | Prenol? Solvent/ Fruity | 3 | OK, Clear | sour solvent | 1 |  |  |  |
| ROSEMARY OIL | 1/510706 | 1.0% | OK, Clear | OK | 3 | OK, Clear | camphor, herbal | 3 | OK, Clear | eucalyptus-like | 4 |

-continued

| | | | | | | | | | | | |
|---|---|---|---|---|---|---|---|---|---|---|---|
| TUNISIA CRESSANTHER | 3/045062 | 1.0% | OK, 5 mm Cloudy Top | OK | 4 | OK, 10 mm cloudy | green, floral | 3 | oK, 3 mm cloudy | green, aldehydic | 1 |
| PETIOLE | 4/780162 | 1.0% | OK, Clear | sharp green | 2 | OK, Clear | plastic, floral, hyacinth | 2 | OK, Clear | green, floral | 3 |
| YSAMBER K | 3/055120 | 1.0% | OK, 5 mm Cloudy Top | sharp woody green | 1 | OK, 20 mm cloudy | woody, amber | 2 | oK, 3 mm cloudy | woody | 2 |
| ALLYL HEPTOATE (C-7) | 4/010500 | 1.0% | OK, sl. Swirly cloudiness | pineapple, fruity | 2 | OK, Hazy throughout | fruity, pineapple | 3 | OK, Clear | pineapple, | 1 |
| ANTHER | 3/912100 | 1.0% | OK, 3 mm cloudy top | Green, harsh | 2 | OK, 10 mm cloudy | green fruity | 3 | oK, 3 mm cloudy | green, floral | 3 |
| EUCALYPTUS GLOBULUS | 1/913422 | 1.0% | OK, Clear | Eucalyptus, camphor | 3 | OK, Clear | camphoric, medicinal | 3 | OK, Clear | camphor, eucalyptus | 1 |
| MAYOL | 3/954401 | 1.0% | OK, 20 mm cloudy | Floral, green, weak | 2 | ok, 30 mm cloudy | sharp green floral woody | 2 | OK, 10 mm cloudy | green, floral | 2 |
| CEDRAMBER | 3/018911 | 1.0% | OK, 15 mm Cloudy | harsh woody | 2 | OK, 20 mm cloudy | sharp woody cedar | 2 | OK, 5 mm cloudy | woody, amber | 3 |
| CEDROL LIQUID 10% in DPG | 3/019281 | 1.0% | OK, Clear | woody, cedar | 2 | OK, Clear | sl. Woody | 3 | OK, Clear | woody | 4 |
| TONALID, 10% in DPG | 3/976500 | 1.0% | OK, Clear | musk | 2 | OK, Clear | musk | 1 | OK, Clear | musk, tonalid | 3 |
| GALAXOLIDE 50 DEP | 4/900551 | 1.0% | OK, Clear | musk | 3 | OK, Clear | musk | 2 | OK, Clear | musk, sweet | 3 |
| PHENAFLEUR | 3/964150 | 1.0% | OK, 10 mm Cloudy top | rose, green | 3 | OK, Cloudy | sharp green | 2 | OK, 2 mm cloudy | rose, green | 3 |
| TRIDECENE-2-NITRILE | 3/076791 | 1.0% | OK, 10 mm Cloudy top | citrus, nitrile | 2 | OK, 10 mm cloudy | sharp, nitrile | 3 | OK, 5 mm cloudy | citrus, nitrile | 2 |
| CLONAL | 3/923790 | 1.0% | OK, 10 mm Cloudy top | citrus, nitrile | 4 | OK, 10 mm cloudy | sharp nitrile | 1 | OK, 5 mm cloudy | citrus, nitrile, green | 3 |
| VELOUTONE | 4/949088 | 1.0% | OK, sl. Haze | celery, jasmin | 4 | OK, 3 mm cloudy cloudy top | jasmin | 2 | OK, swirly | jasmine, floral | 3 |
| METHYL NAPHTHYL KETONE 10% dpg | 4/933020 | 1.0% | OK, Clear | orange flower | 2 | OK, Clear | orange flower | 2 | OK, Clear | orange flower | 1 |
| NEROLIN YARA YARA 10% dpg | 3/959050 | 1.0% | OK, Clear | orange flower | 3 | OK, Clear | Nerolin | 3 | OK, Clear | orange flower | 1 |
| SANDRANOL | 3/070540 | 1.0% | OK, 10 mm Cloudy top | sandal wood | 4 | OK, 10 mm cloudy | sandal | 3 | OK, 15 mm cloudy | sandal wood | 4 |
| CISTULATE 09126 | 3/920335 | 1.0% | OK, 3 mm cloudy top | piney, green | 3 | OK, 1 mm cloud | woody | 2 | OK, 1 mm cloudy | sour, citrus, woody | 2 |
| PADMA | 3/064461 | 1.0% | OK, Clear | green, hyacinth | 3 | OK, Clear | hyacinth | 4 | OK, Clear | green sharp | 3 |
| METHYL CHAVICOL | 4/131155 | 1.0% | OK, 3 mm cloudy | anise | 4 | OK, 5 mm Cloudy | licorice, basil | 2 | OK, cloudy | licorice, herbal | 2 |

-continued

| Material | Number | % | Color/Physical | RM Odor | NH3 Coverage | Color/Physical | RM Odor | NH3 Coverage | Color/Physical | RM Odor | NH3 Coverage |
|---|---|---|---|---|---|---|---|---|---|---|---|
| RHUBAFURAN | 4/941135 | 1.0% | top OK, Clear | aldehydic, woody | 2 | top OK, Clear | green, woody, aldehydic | 4 | OK, clear | green, plastic | 2 |
| RHUBOFIX | 3/971450 | 1.0% | OK, 3 mm cloudy top | aldehydic, green woody, floral | 3 | OK, 1 mm cloud | green, woody, lactonic | 2 | OK, cloudy | green, sharp | 4 |
| DELPHONE, FIRMENICH | 4/916128 | 1.0% | OK, hazy | jasmone | 4 | OK, 1 mm cloud | jasmine, fruity | 4 | OK, cloudy | celery | 4 |
| GRAPEFRUIT BASE 15.794 B | 0/115317 | 1.0% | OK, Clear | woody, grapefruit | 1 | OK, Clear | sl grapefruit | 1 | OK, Clear | grapefruit | 2 |
| ORANGE JUICE CARBONYLS | 4/777119 | 1.0% | OK, Clear | OK, orange, sweet | 3 | ok. sl milky | orange, v sl sour aldehydic | 3 | OK, Clear | fruity, orange | 2 |
| CAMPHENE | 4/726750 | 1.0% | OK, Clear | pine, diffusive | 2 | OK, Clear | camphene, pine | 3 | OK, Clear | aromatic, pine | 4 |
| BENZALDEHYE | 3/914590 | 1.0% | OK, Clear | flat, not typical | 3 | OK, clear | changed, not unpleasant | 4 | OK, Clear | sl. Fruity? | 4 |

| | | | 1 Week, 25 C | | | 2 Week, 25 C | | | 3 Week, 25 C | | |
|---|---|---|---|---|---|---|---|---|---|---|---|
| Material | Number | % | Color/Physical | RM Odor | NH3 Coverage | Color/Physical | RM Odor | NH3 Coverage | Color/Physical | RM Odor | NH3 Coverage |
| Orange Oil Florida | 4/777160 | 1.0% | As RM, Clear | OK | 1 | OK, Clear | lemon, citrus, changed, lower impact | 2 | OK, Clear | aldehydic, fruity | 3 |
| Diola | 3/926899 | 1.0% | OK, Clear | OK | 5 | OK, Clear | banana, green | 4 | OK, Clear | green, banana | 3 |
| Ethyl Acetoacetate | 4/910050 | 1.0% | OK, Clear | OK, low | 2 | OK, Clear | sour, fruity | 2 | OK, clear | sour solventy | 1 |
| Lilial | 4/929325 | 1.0% | OK, Clear | Oxidized | 3 | OK, Clear | faint floral | 3 | OK, Clear | sour, oxidized | 2 |
| Hexyl cinnamic Aldehyde | 3/011371 | 1.0% | OK, Clear | Changed, sour Acidic | 3 | OK, Clear | floral | 3 | OK, Clear | low | 2 |
| Tetrahydro-linalool | 3/034395 | 1.0% | OK, Clear | OK | 2 | OK, v. sl hazy | green floral | 3 | OK, Clear | floral | 2 |
| Florazone | 3/034395 | 1.0% | OK, Clear | OK | 4 | OK, Clear | green, floral, plastic | 3 | OK, Clear | floral, v sl sour plastic | 3 |
| Iso E Super | 0/115115 | 1.0% | OK, Clear | OK | 3 | OK, clear | woody | 4 | Dark, Clear | woody | 3 |
| Iso Bornyl Acetate | 3/943760 | 1.0% | OK, Clear | OK/ Sl Borneol-like | 4 | OK, clear | borneol-ish | 2 | OK, Clear | borneol | 1 |
| Phenyl Ethyl Alcohol | 3/964540 | 1.0% | OK, Clear | OK | 5 | OK, Clear | rose, green | 4 | OK, Clear | green, rose, floral | 4 |
| Dihydro Terpineol | 4/016236 | 1.0% | OK, Clear | OK | 1 | sl. Darker, Clear | sour, burning | 1 | OK, Clear | floral, plastic, sour | 1 |
| Ylanat Ortho | 3/084027 | 1.0% | OK, Clear | Woody/ Green | 2 | OK, Clear | sour, sharp | 2 | OK, Clear | woody, green, sharp | 2 |
| Ylanat | 3/084021 | 1.0% | OK, Clear | Woody/ Green | 2 | OK, Clear | sour | 1 | OK, Clear | woody, green, sharp | 2 |
| Melonal | 3/054211 | 1.0% | OK, Clear | Sour, Fruity | 3 | OK, Clear | plasticky | 1 | OK, Clear | plastic, sour, sharp | 1 |
| Methyl Ionone Gamma | 4/931205 | 1.0% | OK, Clear | OK | 4 | Darker, Clear | woody | 2 | Dar, Clear | Ionone, weak | 2 |
| ALLYL CYCLOHEXYL PROPIONATE | 3/011241 | 1.0% | OK, Clear | OK | 3 | OK, Clear | fruity, pineapple sharp | 2 | OK, clear | pineapple, fruity | 3 |
| CYCLOHEXYL | 3/934060 | 1.0% | OK, | OK | 2 | OK, | floral, | 3 | OK, | green, | 1 |

-continued

| | | | | | | | | | | | |
|---|---|---|---|---|---|---|---|---|---|---|---|
| ETHANOL | | | Clear | | | Clear | green, plastic | | Clear | floral, fruity | |
| FLOROL | 3/934060 | 1.0% | OK, Clear | OK | 3 | OK, Clear | floral, muguet | 4 | OK, Clear | jasmine, floral | 2 |
| GERANYL ACETATE | 3/039991 | 1.0% | OK, Clear | Geraniol | 2 | OK, Clear | weak geraniol | 1 | | | |
| PRENYL ACETATE | 3/026832 | OK, Solvent, Clear | | 1 Sour, Fruity | OK, sour Clear | | 1 solvent | | | | |
| ROSEMARY OIL TUNISIA | 1/510706 | 1.0% | OK, Clear | OK, camphor/ eucal yptus | 3 | OK, Clear | camphoric | 2 | OK, Clear | camphor, eucal lptus | 2 |
| CRESSANTHER | 3/045062 | 1.0% | OK, Clear | OK, sweet, green, floral | 4 | OK, Clear | green, floral | 3 | OK, Clear | green aldehydic | 1 |
| PETIOLE | 4/780162 | 1.0% | OK, Clear | sharp green | 3 | OK, Clear | green, floral | 3 | OK, Clear | green, floral | 3 |
| YSAMBER K | 3/055120 | 1.0% | OK, Clear | green woody | 3 | OK, Clear | woody, sour | 2 | OK, Clear | woody, timberol- like | 1 |
| ALLYL HEPTOATE (C-7) | 4/010500 | 1.0% | OK, Clear | fruity pineapple | 4 | OK, Clear | fruity, pineapple | 2 | OK, Clear | fruity, pineapple | 2 |
| ANTHER | 3/912100 | 1.0% | OK, Clear | green floral harsh | 2 | OK, Clear | green, fruity, woody | 2 | OK, Clear | green, floral | 2 |
| EUCALYPTUS GLOBULUS | 1/913422 | 1.0% | OK, Clear | eucal yptus, camphoric | 1 | OK, Clear | camp horic, medicinal | 3 | OK, Clear | eucal yptus | 1 |
| MAYOL | 3/954401 | 1.0% | OK, 10 mm Cloudy | green floral, weak | 3 | OK, 25 mm Cloudy | sharp green plastic | 2 | OK, 10 mm cloudy | green, floral | 1 |
| CEDRAMBER | 3/018911 | 1.0% | OK, Clear | woody, cedar | 3 | OK, Clear | woody, sharp | 2 | OK, Clear | woody, amber | 2 |
| CEDROL LIQUID 10% in DPG | 3/019281 | 1.0% | OK, Clear | woody, cedar | 4 | OK, Clear | woody | 3 | OK, Clear | woody, flat | 3 |
| TONALID, 10% in DPG | 3/976500 | 1.0% | OK, Clear | musk | 1 | OK, Clear | tonalid | 2 | OK, Clear | musk, tonalid | 2 |
| GALAXOLIDE 50 DEP | 4/900551 | 1.0% | OK, Clear | musk | 3 | OK, Clear | galax olide | 3 | OK, Clear | musk, galax olide | 3 |
| PHENAFLEUR | 3/964150 | 1.0% | OK, Clear | rose, green | 2 | OK, Clear | sharp green | 2 | OK, Clear | rose, green | 3 |
| TRIDECENE-2- NITRILE | 3/076791 | 1.0% | OK, 3 mm Cloudy top | citrus, nitrile | 3 | OK, cloudy top | nitrile, sl. Sour | 3 | OK, sl swirly cloudy | citrus, nitrile | 3 |
| CLONAL | 3/923790 | 1.0% | OK, 8 mm Cloudy top | citrus, nitrile | 4 | OK, 10 mm cloudy top | nitrile | 2 | OK, 5 mm cloudy | citrus, nitrile, green | 3 |
| VELOUTONE | 4/949088 | 1.0% | OK, Clear | fruity, jasmine, celery | 2 | OK, Clear | jasmine | 3 | OK, Clear | jasmine, green | 2 |
| METHYL NAPHTHYL KETONE 10% dpg | 4/933020 | 1.0% | OK, Clear | orange flower | 3 | OK, Clear | low | 2 | OK, Clear | orange flower, sweet | 2 |
| NEROLIN YARA YARA 10% dpg | 3/959050 | 1.0% | OK, Clear | orange flower | 3 | | nerolin | 3 | OK, Clear | orange flower, sweet | 3 |
| SANDRANOL | 3/070540 | 1.0% | OK, 10 mm Cloudy | very strong sandal | 2 | OK, 10 mm cloudy top | sandal wood | 3 | OK, 20 mm cloudy | sandal wood | 3 |
| CISTULATE 09126 | 3/920335 | 1.0% | OK, Clear | sweet, woody | 3 | OK, Clear | woody, naphthyl | 3 | OK, Clear | woody, sour | 2 |
| PADMA | 3/064461 | 1.0% | OK, Clear | green, hyacinth | 3 | OK, Clear | hyacinth | 4 | OK, Clear | green sharp | 3 |
| METHYL CHAVICOL | 4/131155 | 1.0% | OK, Clear | anise | 2 | OK, Clear | licorice, herbal | 2 | OK, Clear | licorice, herbal | 2 |
| RHUBAFURAN | 4/941135 | 1.0% | OK, Clear | aldehydic, green, | 2 | OK, Clear | green, woody, | 3 | OK, Clear | green, plastic | 2 |

-continued

| | | | | | | | | | | | |
|---|---|---|---|---|---|---|---|---|---|---|---|
| RHUBOFIX | 3/971450 | 1.0% | OK, Clear | sharp green, floral | 2 | OK, Clear | aldehydic sharp green | 3 | OK, Clear | green, sharp, aldehydic | 4 |
| DELPHONE FIRMENICH GRAPEFRUIT BASE 15.794 B ORANGE JUICE CARBONYLS CAMPHENE BENZALDEHYE | 4/916128 | 1.0% | OK, Clear | jasmone | 4 | OK, Clear | fruity, jasmine | 3 | OK, Clear | jasmine | 4 |

| Material | Number | % | 1 Week, 38 C Color/ Physical | 1 Week, 38 C RM Odor | 1 Week, 38 C NH3 Coverage | 1 Week Avg NH3 Cover | 2 week Avg NH3 Cover | 3 week Avg NH3 Cover |
|---|---|---|---|---|---|---|---|---|
| Orange Oil Florida | 4/777160 | 1.0% | As RM, sl. Cloudiness | Flat Aldehydic | 1 | 1 | 3 | 3 |
| Diola | 3/926899 | 1.0% | OK, Clear | OK | 5 | 5 | 4 | 4 |
| Ethyl Acetoacetate | 4/910050 | 1.0% | OK, Clear | Sour, Acidic | 1 | 2 | 2 | 1 |
| Lilial | 4/929325 | 1.0% | OK, Clear | Oxidized | 4 | 3 | 3 | 2 |
| Hexyl cinnamic Aldehyde | 3/011371 | 1.0% | OK, Clear | Sl changed | 2 | 2 | 3 | 2 |
| Tetrahydro- linalool | 4/901360 | 1.0% | OK, Clear | OK | 2 | 2 | 3 | 3 |
| Florazone | 3/034395 | 1.0% | OK, Clear | OK | 4 | 4 | 4 | 3 |
| Iso E Super | 0/115115 | 1.0% | Yellower, Clear | OK | 3 | 3 | 4 | 3 |
| Iso Bornyl Acetate | 3/943760 | 1.0% | OK, Clear | OK to Borneol | 3 | 3 | 3 | 2 |
| Phenyl Ethyl Alcohol | 3/964540 | 1.0% | OK, Clear | OK | 4 | 4 | 5 | 4 |
| Dihydro Terpineol | 4/016236 | 1.0% | OK, Clear | OK? | 1 | 2 | 2 | 2 |
| Ylanat Ortho | 3/084027 | 1.0% | Yellower, Clear | Woody/ Green | 3 | 3 | 2 | 3 |
| Ylanat | 3/084021 | 1.0% | Yellower, Clear | Woody/ Green | 2 | 2 | 2 | 3 |
| Melonal | 3/054211 | 1.0% | OK, Clear | Sour, acidic, plastic | 3 | 3 | 1 | 2 |
| Methyl Ionone Gamma | 4/931205 | 1.0% | Yellower, Clear | OK | 4 | 4 | 3 | 3 |
| ALLYL CYCLOHEXYL PROPIONATE | 3/011241 | 1.0% | OK, Clear | sl. Sour, mostly OK | 2 | 2 | 3 | 3 |
| CYCLOHEXYL ETHANOL | 3/924060 | 1.0% | OK, Clear | Sour | 1 | 1 | 3 | 2 |
| FLOROL | 3/934060 | 1.0% | OK, Clear | OK | 3 | 3 | 4 | 2 |
| GERANYL ACETATE | 3/039991 | 1.0% | OK, Clear | Geraniol/ Nerol | 2 | 2 | 1 | 0 |
| PRENYL ACETATE | 3/026832 | 1.0% | OK, Clea | Plastic/ Solvent | 1 | 2 | 1 | 0 |
| ROSEMARY OIL TUNISIA | 1/510706 | 1.0% | OK, Clear | camphor/ eucalytus | 1 | 2 | 3 | 3 |
| CRESSANTHER | 3/045062 | 1.0% | OK, Clear | green, floral | 2 | 3 | 3 | 1 |
| PETIOLE | 4/780162 | 1.0% | OK, Clear | green, aldehydic | 2 | 2 | 3 | 3 |
| YSAMBER K | 3/055120 | 1.0% | OK, | sl. | 1 | 2 | 2 | 2 |

-continued

| | | | | | | | | |
|---|---|---|---|---|---|---|---|---|
| | | | Clear | Woody, not stable | | | | |
| ALLYL HEPTOATE (C-7) | 4/010500 | 1.0% | OK, Clear | fruity, pineapple | 2 | 3 | 3 | 2 |
| ANTHER | 3/912100 | 1.0% | OK, Clear | green floral | 1 | 2 | 3 | 3 |
| EUCALYPTUS GLOBULUS | 1/913422 | 1.0% | OK, Clear | very camp horac eous | 1 | 2 | 3 | 1 |
| MAYOL | 3/954401 | 1.0% | OK, hazy | green floral weak | 3 | 3 | 2 | 2 |
| CEDRAMBER | 3/018911 | 1.0% | OK, Clear | woody, cedar | 1 | 2 | 2 | 3 |
| CEDROL LIQUID 10% in DPG | 3/019281 | 1.0% | OK, Clear | woody, cedar | 4 | 3 | 3 | 4 |
| TONALID, 10% in DPG | 3/976500 | 1.0% | OK, Clear | musk | 1 | 1 | 2 | 3 |
| GALAXOLIDE 50 DEP | 4/900551 | 1.0% | OK, Clear | musk | 2 | 3 | 3 | 3 |
| PHENAFLEUR | 3/964150 | 1.0% | OK, Clear | green rose | 2 | 2 | 2 | 3 |
| TRIDECENE-2-NITRILE | 3/076791 | 1.0% | OK, Clear | citrus, nitrile, sl. Sour | 3 | 3 | 3 | 3 |
| CLONAL | 3/923790 | 1.0% | OK, Clear | citrus, nitrile, lemon | 3 | 4 | 2 | 3 |
| VELOUTONE | 4/949088 | 1.0% | OK, Clear | fruity, jasmine | 3 | 3 | 3 | 3 |
| METHYL NAPHTHYL KETONE 10% dpg | 4/933020 | 1.0% | OK, clear | orange flower, weak | 2 | 2 | 2 | 2 |
| NEROLIN YARA YARA 10% dpg | 3/959050 | 1.0% | OK, Clear | orange flower | 2 | 3 | 3 | 2 |
| SANDRANOL | 3/070540 | 1.0% | OK, 15 mm cloudy | sandal wood | 3 | 3 | 3 | 4 |
| CISTULATE 09126 | 3/920335 | 1.0% | OK, Clear | state plastic woody | 3 | 3 | 3 | 2 |
| PADMA | 3/064461 | 1.0% | OK, Clear | green | 3 | 3 | 4 | 3 |
| METHYL CHAVICOL | 4/131155 | 1.0% | OK, Clear | licorice, anise | 3 | 3 | 2 | 2 |
| RHUBAFURAN | 4/941135 | 1.0% | OK, Clear | aldehydic, herbal | 2 | 2 | 4 | 2 |
| RHUBOFIX | 3/971450 | 1.0% | OK, Clear | green, aldehydic | 2 | 2 | 3 | 4 |
| DELPHONE FIRMENICH | 4/916128 | 1.0% | OK, Clear | jasmone | 4 | 4 | 4 | 4 |
| GRAPEFRUIT BASE 15.794 B | 0/115317 | 1.0% | OK, Clear | woody, grapefruit | 2 | 1 | 1 | 1 |
| ORANGE JUICE CARBONYLS | 4/777119 | 1.0% | OK, Clear | orange, flat | 2 | 2 | 2 | 1 |
| CAMPHENE | 4/726750 | 1.0% | OK, Clear | flat pine | 3 | 2 | 2 | 2 |
| BENZALDEHYE | 3/914590 | 1.0% | OK, Clear | not typical | 3 | 2 | 2 | 2 |

| Material | Dragoco Number | Group | Olfactive Stability | Air Diffusion Coeffiecient | Average Coverage | Phenyl Ring Moiety? | C-5 ring with at least 1 sp2 carbon |
|---|---|---|---|---|---|---|---|
| ALLYL CYCLOHEXYL PROPIONATE | 3/011241 | 4 | marginal | 4.86 | 2.6 | N | N |
| ALLYL HEPTOATE (C-7) | 4/010500 | 5 | stable | 5.23 | 2.6 | N | N |
| ANTHER | 3/912100 | 6 | stable | 4.86 | 2.6 | Y | N |
| BENZALDEHYDE* | 3/914590 | 10 | stable* | 7.5 | 3.5 | Y | N |
| CAMPHENE* | 4/726750 | 10 | marginal | 6.13 | 3.0 | N | N |
| CEDRAMBER | 3/018911 | 6 | stable | n/a | 2.3 | N | N |
| CEDROL LIQUID 10% | 3/019281 | 6 | stable | 4.25 | 3.3 | N | N |
| CISTULATE 09126 | 3/920335 | 8 | not stable | n/a | 2.6 | N | N |
| CLONAL | 3/923790 | 7 | stable | 4.66 | 3.0 | N | N |
| CRESSANTHER | 3/045062 | 5 | stable | n/a | 2.3 | Y | N |
| CYCLOHEXYL ETHANOL | 3/924060 | 4 | stable | 6.29 | 2.0 | N | N |
| DELPHONE, FIRMENICH | 4/916128 | 9 | stable | 5.46 | 4.0 | N | Y |
| DIHYDRO TERPINEOL | 4/016236 | 3 | not stable | 5.47 | 2.0 | N | N |
| DIOLA | 3/926899 | 1 | stable | 6.51 | 4.3 | N | N |
| ETHYL ACETOACETATE | 4/910050 | 1 | not stable | 5.54 | 1.6 | N | N |
| EUCALYPTUS GLOBULUS | 1/913422 | 6 | stable | n/a | 2.0 | N | N |
| FLORAZONE | 3/034395 | 2 | marginal | 4.99 | 3.6 | Y | N |
| FLOROL | 3/934060 | 4 | stable | 5.21 | 3.0 | N | N |
| GALAXOLIDE 50 DEP 10% | 4/900551 | 7 | stable | 4.07 | 3.0 | N | N |
| GERANYL ACETATE | 3/039991 | 4 | not stable | 4.78 | 1.0 | N | N |
| GRAPEFRUIT BASE 15.794 B* | 0/115317 | 10 | stable | n/a | 1.5 | U | U |
| HEXYL CINNAMIC ALDEHYDE | 3/011371 | 1 | not stable | 4.45 | 2.3 | Y | N |
| ISO BORNYL ACETATE | 3/943760 | 2 | not stable | 4.92 | 2.6 | N | N |
| ISO E SUPER | 0/115115 | 2 | not stable | 4.18 | 3.3 | N | N |
| LILIAL | 4/929325 | 1 | not stable | 4.7 | 2.6 | Y | N |
| MAYOL | 3/954401 | 6 | not stable | 5.45 | 2.3 | N | N |
| MELANOL | 3/054211 | 3 | not stable | 5.79 | 2.0 | N | N |
| METHYL CHAVICOL | 4/131155 | 9 | not stable | 5.91 | 2.3 | Y | N |
| METHYL IONONE GAMMA | 4/931205 | 3 | marginal | 4.53 | 3.3 | N | N |
| METHYL NAPHTHYL KETONE 10% | 4/933020 | 8 | stable | 5.52 | 2.0 | Y | N |
| NEROLIN YARA YARA 10% | 3/959050 | 8 | stable | 5.84 | 2.6 | Y | N |
| ORANGE JUICE CARBONYLS* | 4/777119 | 10 | stable | n/a | 2.5 | N | N |
| ORANGE OIL FLORIDA | 4/777160 | 1 | not stable | n/a | 2.3 | U | U |
| PADMA | 3/064461 | 9 | stable | 5.71 | 3.3 | Y | N |
| PETIOLE | 4/780162 | 5 | marginal | n/a | 2.6 | Y | N |
| PHENAFLEUR | 3/964150 | 7 | stable | 4.77 | 2.3 | Y | N |
| PHENYL ETHYL ALCOHOL | 3/964540 | 2 | stable | 6.76 | 4.3 | Y | N |
| PRENYL ACETATE | 3/026832 | 4 | not stable | 6.49 | 1.0 | N | N |
| RHUBAFURAN | 4/941135 | 9 | not stable | n/a | 2.6 | Y | N |
| RHUBOFIX | 3/971450 | 9 | not stable | n/a | 3.0 | N | N |
| ROSEMARY OIL TUNISIA | 1/510706 | 5 | stable | n/a | 2.6 | N | N |
| SANDRANOL | 3/070540 | 8 | stable | 4.44 | 3.3 | N | Y |
| TETRAHYDRO LINALOOL | 4/901360 | 2 | stable | 5.33 | 2.6 | N | N |
| TONALID 10% | 3/976500 | 7 | stable |  | 2.0 | N | N |
| TRIDECENE-2-NITRILE | 3/076791 | 7 | not stable | 4.32 | 3.0 | N | N |
| VELOUTONE | 4/949088 | 8 | stable | 4.59 | 3.0 | N | Y |
| YLANAT | 3/084021 | 3 | not stable | 4.79 | 2.3 | N | N |
| YLANAT ORTHO | 3/084027 | 3 | not stable | 4.77 | 2.6 | N | N |
| YSAMBER K | 3/055120 | 5 | not stable | n/a | 2.0 | N | N |

* = tested only at 5 and 38 C   * = changed character, but not offensive

Although this invention has been described in its preferred form with a certain degree of particularity with respect to a method for determining perfumes to be used to mask ammonia in a hair treatment composition, it is understood that the present disclosure of the preferred form has been made only by way of example, and that numerous changes in the details of structures and composition of the product may be resorted to without departing from the spirit and scope of the invention.

What is claimed is:

1. A method for masking the perception of ammonia from an aqueous media comprising:
   providing an aqueous media containing 1–15 wt. % ammonia;
   adding to said aqueous media a sufficient amount of at least one perfume which is olfactively stable in said aqueous media to suppress the perception of ammonia;
   wherein the perfume satisfies one of the following criteria:
   1) contains a phenyl ring moiety and has an air diffusion coefficient of >5.7,
   2) contains a C-5 ring moiety, which also contains at least 1 carbon which is sp2 hybridized, and has an air diffusion coefficient of >4.4.

2. A method as in claim 1, wherein said perfume contains at least 25% of materials satisfying criteria (1) or (2).

3. A method as in claim 1, wherein said aqueous media contains from 5 to 10 wt. % ammonia.

4. A method as in claim 1, wherein said aqueous media is selected from the group consisting of hair colorants and hair bleaches.

5. An ammonia-containing hair treatment composition having reduced ammonia odor, said composition comprising:
   aqueous media containing 1–15% ammonia;
   at least one perfume in sufficient amount to suppress the perception of ammonia;

wherein the perfume is olfactively stable in the aqueous media and satisfies one of the following criteria:
1) contains a phenyl ring moiety and has an air diffusion coefficient of >5.7,
2) contains a C-5 ring moiety, which also contains at least 1 carbon which is sp2 hybridized, and has an air diffusion coefficient of >4.4.

6. An ammonia-containing hair treatment composition as in claim 5, wherein said composition is a hair colorant.

7. An ammonia-containing hair treatment composition as in claim 5, wherein said composition is a hair bleach.

8. An ammonia-containing hair treatment composition as in claim 5, wherein said composition is a gel composition.

* * * * *